(12) United States Patent
Locke

(10) Patent No.: US 6,309,603 B1
(45) Date of Patent: Oct. 30, 2001

(54) MICROCENTRIFUGE TUBE CAP OPENING AND CLOSING APPARATUS AND METHOD

(75) Inventor: H. Charles Locke, Voorhees, NJ (US)

(73) Assignee: Drummond Scientific Company, Broomall, PA (US)

( * ) Notice: Subject to any disclaimer, the term of this patent is extended or adjusted under 35 U.S.C. 154(b) by 0 days.

(21) Appl. No.: 09/241,488

(22) Filed: Feb. 1, 1999

(51) Int. Cl.[7] ....................................................... B67B 7/16
(52) U.S. Cl. ........................... 422/72; 210/360.1; 494/16; 81/3.55
(58) Field of Search ........................... 422/72; 210/360.1; 494/16; 81/3.55

(56) References Cited

U.S. PATENT DOCUMENTS 5,253,551 * 10/1993 DeVaugn ............................... 81/3.55
5,967,001 * 10/1999 Regester ............................... 81/3.55

* cited by examiner

Primary Examiner—David A. Reifsnyder
(74) Attorney, Agent, or Firm—Joseph M. Konieczny; John F. A. Earley; Harding, Earley, Follmer & Frailey

(57) ABSTRACT

A single-hand apparatus for opening and closing the cap of a microcentrifuge tube. The apparatus comprises an elongate base having means on one end for mounting the base on a laboratory ring stand and means on the other end of the base for allowing a technician to hold the microcentrifuge tube in one hand and to open and close the cap without requiring a second hand.

35 Claims, 7 Drawing Sheets

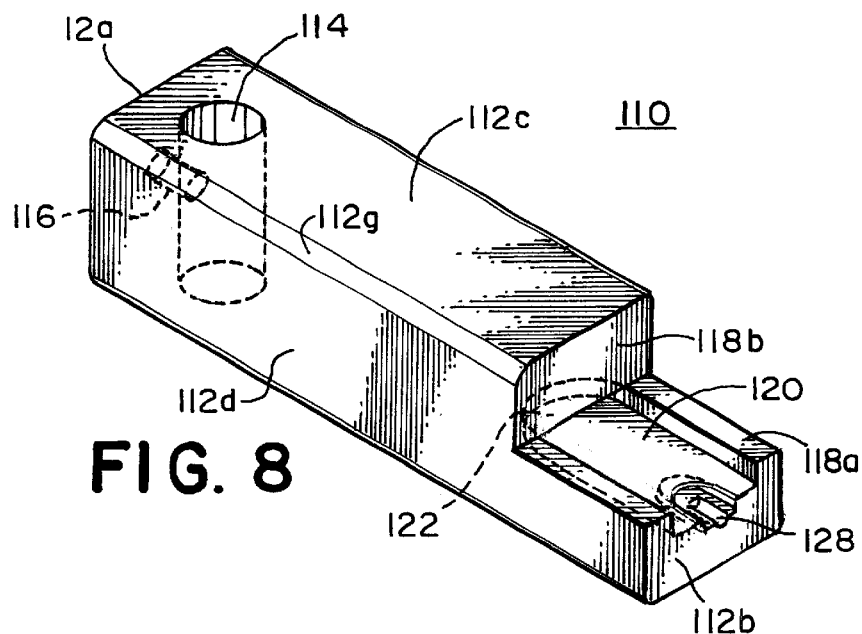
FIG. 8
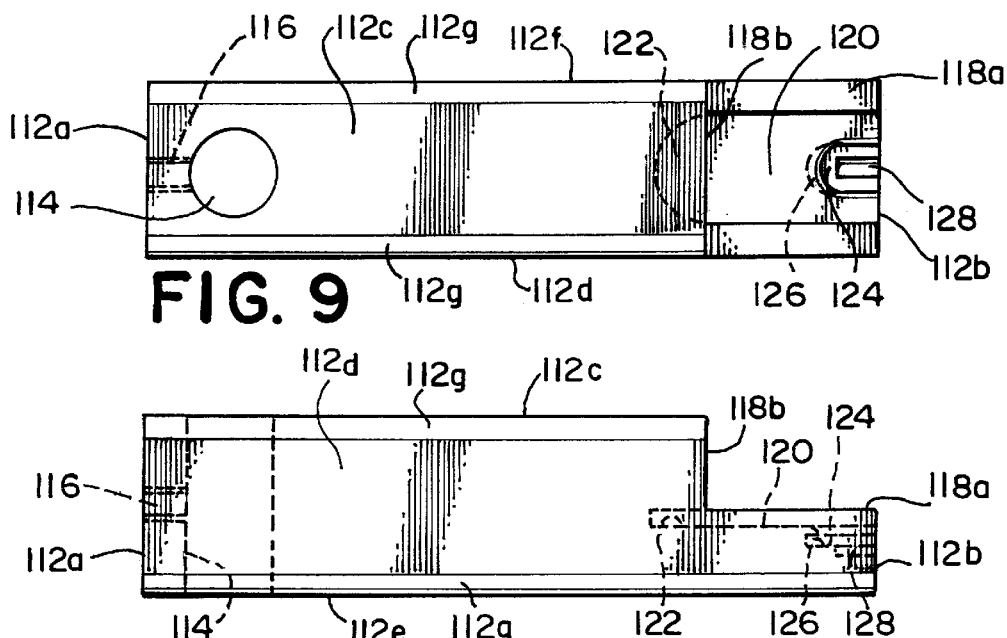
FIG. 9
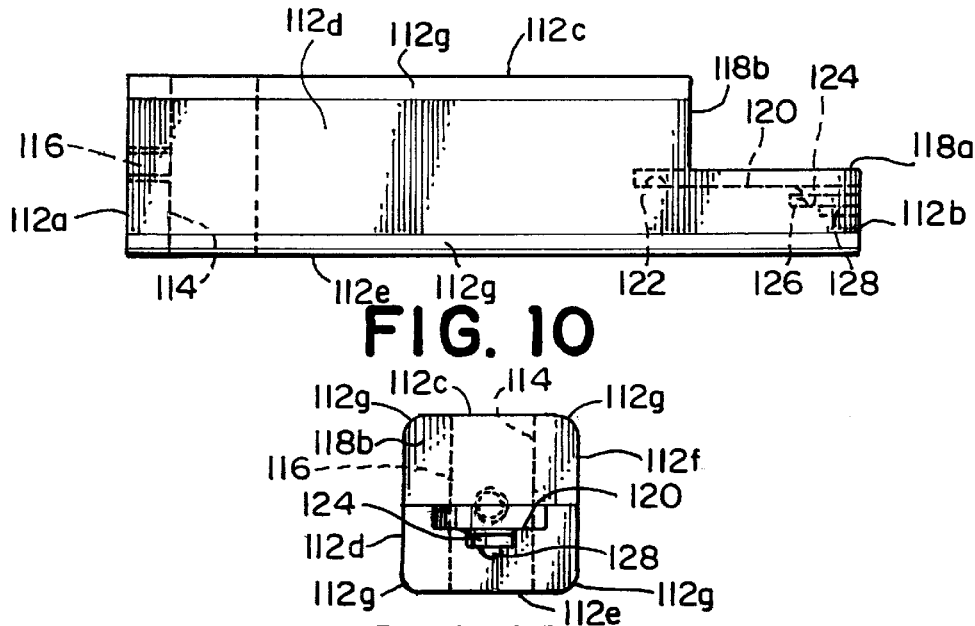
FIG. 10
FIG. 11

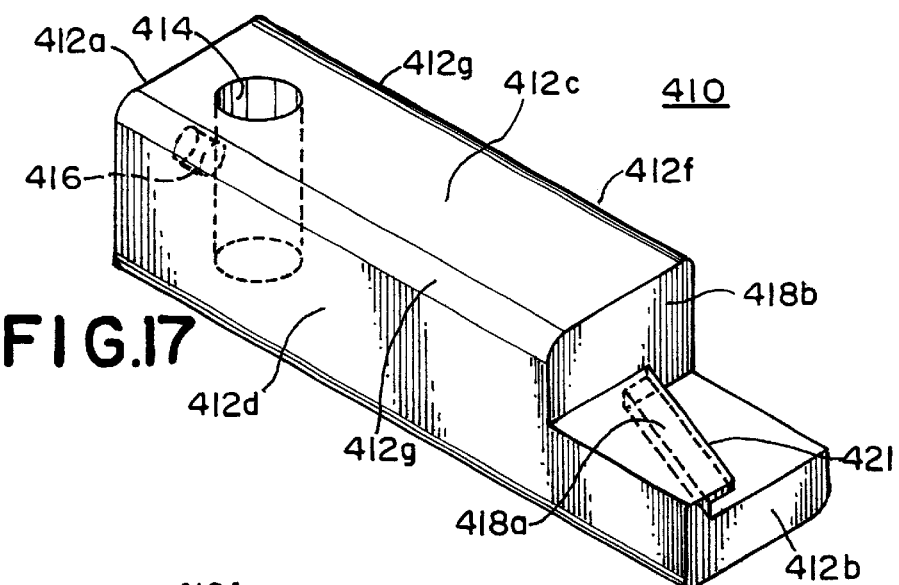
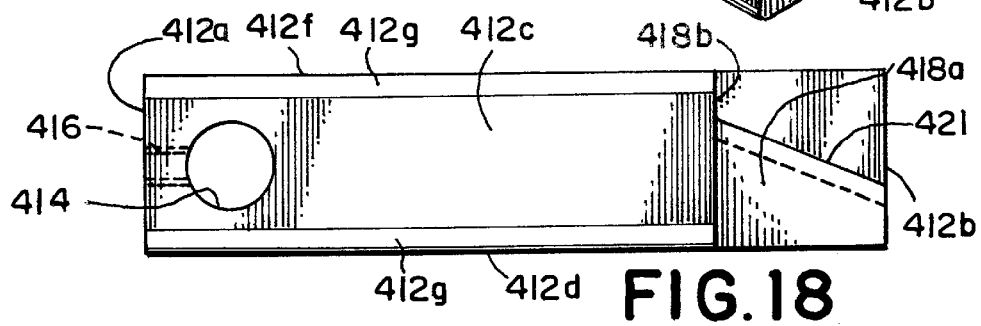
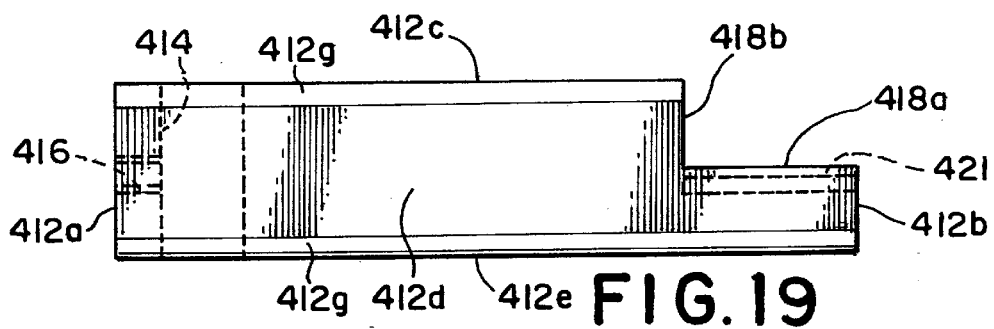
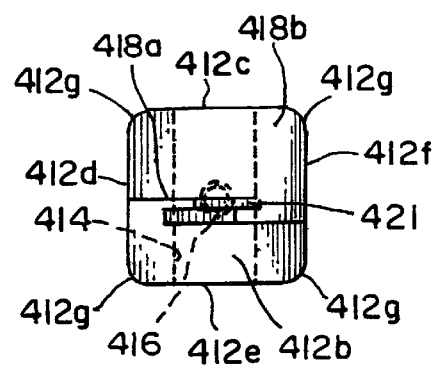

MICROCENTRIFUGE TUBE CAP OPENING AND CLOSING APPARATUS AND METHOD

FIELD OF THE INVENTION

The present invention relates to an apparatus and method which enables a technician to hold a microcentrifuge tube in one hand, and to open and close the cap without requiring a second hand. The present invention also relates to a single apparatus and method which will open and close a plurality of different size tube caps.

BACKGROUND OF THE INVENTION

Microcentrifuge tubes are commonly used for a wide variety of tests which require only small amounts of test fluid. Microcentrifuge tubes typically have a hinged snap cap such as illustrated in FIGS. 1 and 2. Due to its very small size, grasping a microcentrifuge tube, and opening or closing its tightly-fitting snap cap, is difficult, especially for a technician having larger than average hands.

During research or testing, a technician typically opens and closes each microcentrifuge tube several times per experiment to add or subtract fluid from the microcentrifuge tube. It is also common for a laboratory or research technician to handle hundreds of microcentrifuge tubes each day. The cumulative effect of repeatedly opening and closing the snap cap of hundreds of microcentrifuge tubes in a single day is often fatigue or injury to the technician. Therefore, it would be desirable to provide an apparatus for opening and closing the cap of a microcentrifuge tube to reduce fatigue or injury to the technician.

Microcentrifuge tubes are provided in a plurality of sizes, each of which has a different size cap. It is common for a technician to handle concurrently a wide range of different size microcentrifuge tubes. Therefore, it would also be desirable to provide a single apparatus which will open and close a plurality of different size microcentrifuge tubes.

During testing or experimentation, a technician routinely opens a microcentrifuge tube, meters fluid to or from the tube using a pipette gun, and then closes the tube for subsequent centrifuging. To manually open the snap cap of a microcentrifuge tube, a technician must grasp the tube with a first hand and prye open the cap with a second hand. To meter fluid to or from the microcentrifuge tube, the technician holds the tube in a first hand and holds the pipette gun in a second hand. Each time the tube is opened or closed using the above-described two-hand manual operation, the technician must set the pipette gun down on the laboratory bench. The cumulative effect of the added step of repeatedly picking up and setting down the pipette gun in order to open and then close hundreds of microcentrifuge tubes in a single day further adds to the fatigue or injury to the technician. Therefore, it would be desirable to provide an apparatus which enables a technician to hold the microcentrifuge tube in one hand, and to open and close the cap of the tube without requiring a second hand.

SUMMARY OF THE INVENTION

The present invention provides an apparatus for opening and closing the cap of a microcentrifuge tube to reduce fatigue or injury to the technician. The apparatus will open and close a plurality of different size microcentrifuge tubes. The apparatus enables a technician to hold the microcentrifuge tube in one hand, and to open and close the cap of the tube without requiring a second hand.

A first embodiment of the invention enables a technician to open and close a cap having a diameter D. The single-hand apparatus of the present invention has an elongate base having first and second end surfaces. A plurality of side surfaces extend intermediate the end surfaces. The base preferably comprises an elongate bar having a square cross section.

The base may also have a two-part construction. In this embodiment, the two base is split into two pivotally-connected halves.

A first cylindrical bore is located proximate the first end surface and extends through the base transverse to the lengthwise axis. The first cylindrical bore has a diameter slightly larger than the diameter of the upright support rod of a laboratory stand. The base also includes a threaded bore extending from the first end surface to the first cylindrical bore. The threaded bore is constructed to receive a thumb screw which tightens onto the support rod. If it is desired to mount the opener on a horizontally-extending support rod, the opener may include a second cylindrical bore extending through the base transverse to the first bore and the lengthwise axis.

A notch is formed in the base proximate the second end surface. The notch has a horizontal surface extending a distance "Y" generally-parallel to the lengthwise axis, and a vertical surface extending a distance "X" generally-parallel to the end surfaces.

A race is formed in the horizontal notch surface and extends from the second end surface a distance "Z" which is greater than "Y". The race has a uniform width "WR1" slightly larger than the diameter of the cap of the microcentrifuge tube.

A pocket is contiguously formed with the end of the race proximate the intersection of the horizontal and vertical notch surfaces. The pocket has a length "LP1" which is equal to "Z" minus "Y" and a width "WP". The pocket length "LP1" is approximately equal to or greater than the length of the cap lip.

The present invention also provides a single-hand apparatus for opening two different size caps. The opener has an elongate base, means on the first end for mounting the base on a laboratory ring stand, first means on the second end for releasably holding the first size cap without holding the tube, and second means on the second end for releasably holding the second size cap without holding the tube.

The first holding means comprises a notch in the base proximate the second end surface. The notch has a horizontal surface extending a distance "Y" generally-parallel to the lengthwise axis, and a vertical surface extending a distance "X" generally-parallel to the end surfaces. A first race is formed in the horizontal notch surface and extends from the second end surface a distance "Z1" which is greater than "Y". The first race has a width "WR1" slightly larger than the diameter D1 of the first size cap.

A first pocket is contiguously formed with the race proximate the intersection of the horizontal and vertical notch surfaces. The pocket has a length "LP1" which is equal to "Z" minus "Y" and a width "WP". The first pocket length "LP1" is approximately equal to or greater than the length of the lip of the first size cap.

The second holding means comprises a second race formed in the first race. The second race extends from the second end surface a distance "Z2" which is less than "Y". The second race has a width "WR1" slightly larger than the diameter D2 of the second size cap. A groove extends lengthwise down the center of the second race.

A second pocket is contiguously formed with the end of the second race intermediate the horizontal notch surface.

The second pocket has a length "LP2" which is approximately equal to or greater than the length of the lip of the second size cap.

The present invention also provides a single-hand apparatus for opening any size cap within a specified size range. In this embodiment, a notch is formed in the base proximate the second end surface. The notch has a horizontal surface extending a distance "Y" generally-parallel to the lengthwise axis, and a vertical surface extending a distance "X" generally-parallel to the end surfaces.

A single race is formed in the horizontal notch surface. The single race extends and converges in width from the second end surface to the vertical notch surface. The race has a planar bottom surface and side walls generally perpendicular to the bottom surface. One of the race side walls extends parallel to the lengthwise axis. The other race sidewall extends transverse to the lengthwise axis.

An undercut grove is formed in one of the side walls of the race. The undercut groove extends from the second end surface to the vertical notch surface.

The undercut groove is formed in the transverse extending race sidewall. The undercut groove is coplanar with the bottom surface of the race. The undercut groove extends a depth D into the sidewall. The depth D is preferably greater than or equal to the length of the lip of the cap.

The present invention provides a further embodiment for opening any size cap within a specified size range. In this embodiment, a first notch is formed in the base proximate the second end surface. The first notch has a horizontal surface extending a distance "Y" generally-parallel to the lengthwise axis, and a vertical surface extending a distance "X" generally-parallel to the end surfaces.

A second notch is formed in the horizontal notch surface. The second notch has a horizontal surface which extends lengthwise a distance "Y" from the second end surface to the vertical surface of the first notch. The horizontal notch surface also extends widthwise a from one of the base side surfaces to a side wall intermediate the horizontal surface of the first notch. The second notch converges in width from the second end surface to the vertical surface of the first notch. The second notch has a planar bottom surface.

An undercut grove is formed in the side wall of the second notch. The undercut groove is coplanar with the bottom surface of the second notch. The undercut groove extends a depth D into the sidewall. The depth D is preferably greater than or equal to the length of the lip of the cap.

BRIEF DESCRIPTION OF THE DRAWINGS

FIG. 8 is an upside-down, perspective view of a single-hand, microcentrifuge tube cap opener in accordance with an embodiment of the invention;

FIG. 9 is a bottom plan view of the tube cap opener shown in FIG. 8;

FIG. 10 is an upside-down, side elevational view of the tube cap opener shown in FIG. 8;

FIG. 11 is an upside-down, front elevational view of the tube cap opener shown in FIG. 8;

FIG. 17 is an upside-down, perspective view of a single-hand, microcentrifuge tube cap opener in accordance with an embodiment of the invention;

FIG. 18 is a bottom plan view of the tube cap opener shown in FIG. 17;

FIG. 19 is an upside-down, side elevational view of the tube cap opener shown in FIG. 17;

FIG. 20 is an upside-down, front elevational view of the tube cap opener shown in FIG. 17;

DESCRIPTION OF PREFERRED EMBODIMENTS

Figure 1:
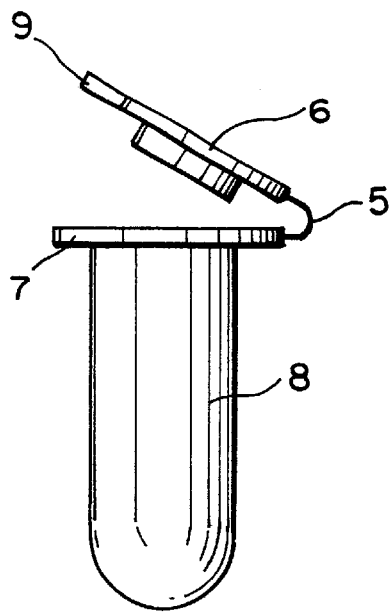
FIG. 1 is a side elevational view of a prior art microcentrifuge tube having a hinged cap shown in an open position.

The single-hand microcentrifuge tube cap opener of the present invention is described below with reference to FIGS. 1–22 wherein like reference numerals are used throughout to designate like elements. As used herein, the term "single-hand" opener refers to an apparatus which enables a technician to hold a microcentrifuge tube in one hand, and to open and close the cap of the tube without requiring a second hand.

Figure 2:
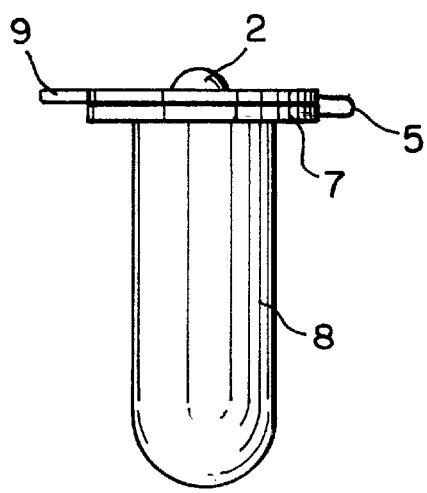
FIG. 2 is a side elevational view of a prior art microcentrifuge tube having a hinged cap shown in a closed position.

The cap opener of the present invention is used for opening and closing the snap cap on a range of different size microcentrifuge tubes. Referring to FIGS. 1 and 2, the microcentrifuge tube assembly generally comprises an elongate tube 8 having an annular rim 7 at the open end. A snap cap 6 having a radially-protruding lip 9 is connected to the annular rim 7 by a hinge 5.

Figure 3:
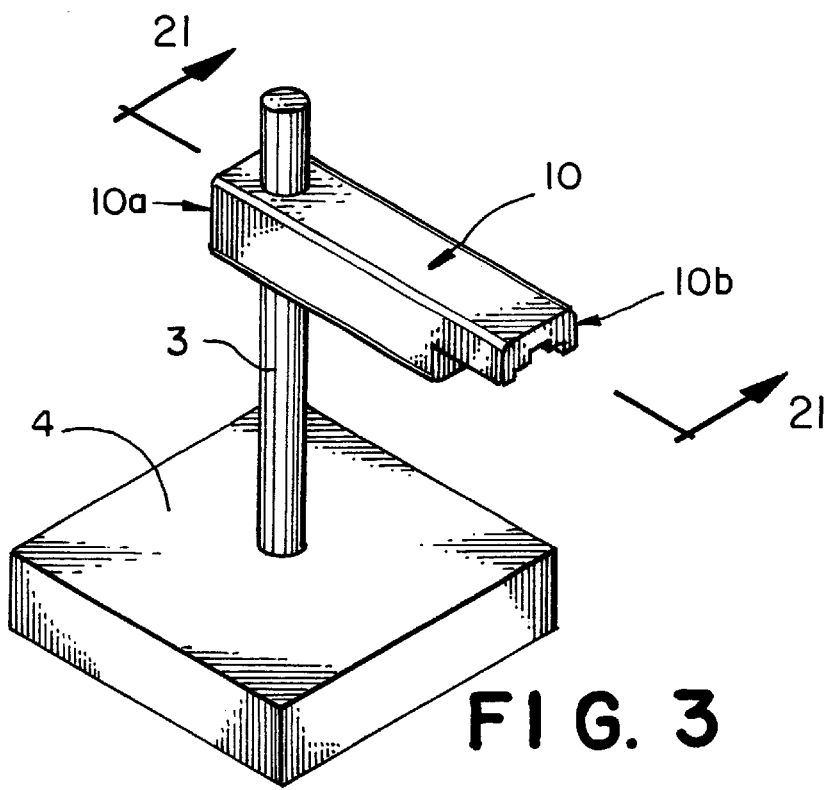
FIG. 3 is a perspective view of a single-hand, microcentrifuge tube cap opener mounted on a laboratory ring stand in accordance with an embodiment of the invention.
Figure 4:
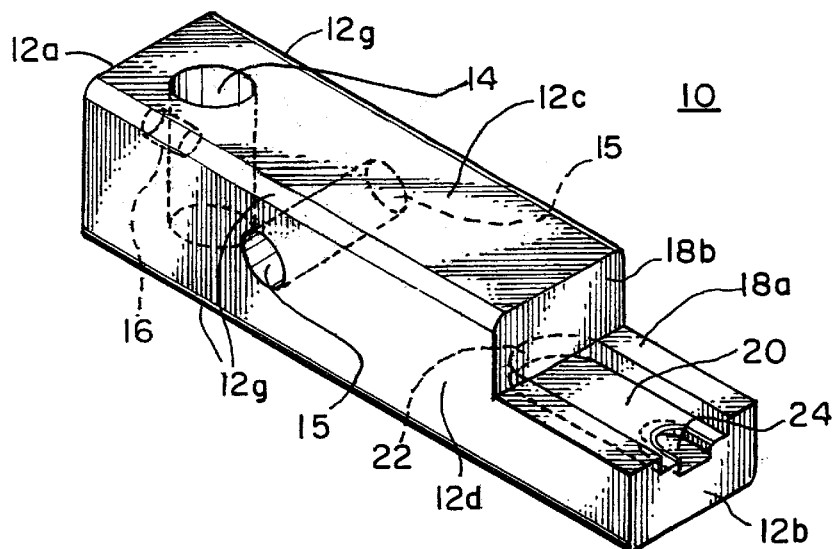
FIG. 4 is an enlarged, upside-down, perspective view of the tube cap opener shown in FIG. 3.
Figure 5:
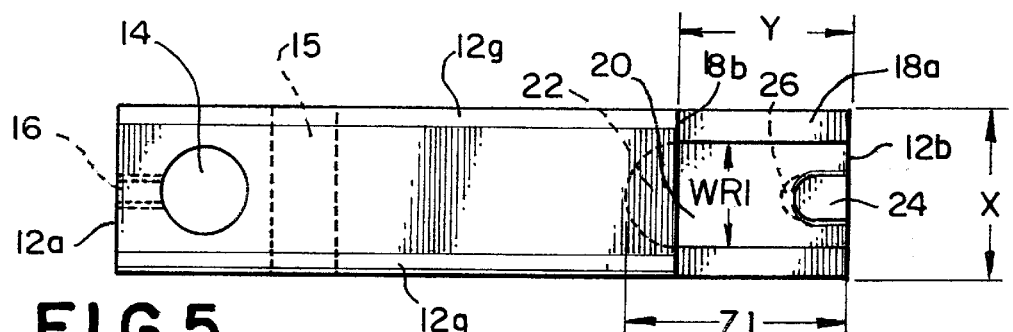
FIG. 5 is a bottom plan view of the tube cap opener shown in FIG. 3.
Figure 6:
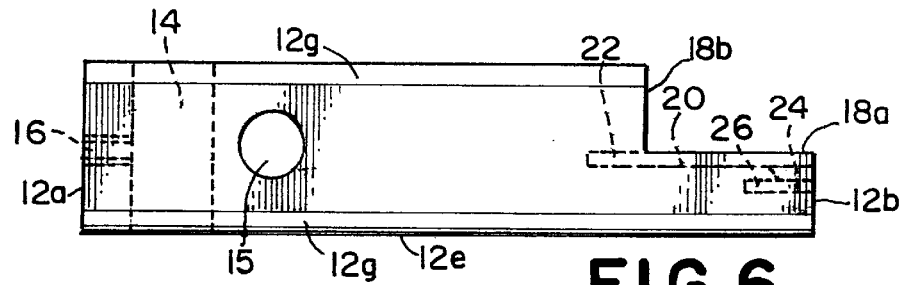
FIG. 6 is an upside-down, side elevational view of the tube cap opener shown in FIG. 3.
Figure 7:
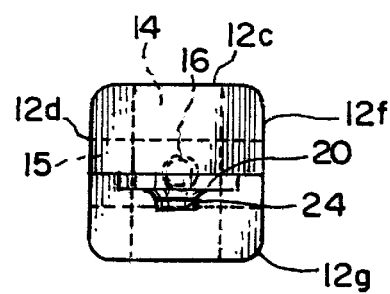
FIG. 7 is an upside-down, front elevational view of the tube cap opener shown in FIG. 3.

A single-hand, microcentrifuge tube cap opener 10 in accordance with an embodiment of the invention is shown in FIG. 3 mounted on a conventional laboratory ring stand having a base 4 and a vertically-extending mounting rod 3. As described in greater detail below, the tube cap opener 10 can be mounted at any height on the vertically-extending mounting rod 3 or, in an alternative embodiment, on a horizontally-extending mounting rod.

Referring to FIGS. 4–7, the tube cap opener 10 has an elongate base 12 having first and second end surfaces 12a, 12b and a plurality of surfaces 12c–12f extending intermediate the end surfaces 12a, 12b. In the embodiment shown in FIGS. 4–7, the base 12 comprises an elongate bar having a generally-square cross section. The four side surfaces 12c–12f have rounded corners 12g at their lengthwise-extending intersection.

The base 12 has means on one end 10a for mounting the base 12 on the vertically-extending mounting rod 3 of a ring stand. In one embodiment, the mounting means comprises a cylindrical bore 14 located proximate the first end surface 12a. The bore 14 extends through the base 12 transverse to the lengthwise axis of the base 12. In the embodiment shown in FIGS. 3–7, the first cylindrical bore 14 extends from the top surface 12c to the bottom surface 12e. If it is desired to mount the opener 10 on a horizontally-extending ring stand support rod, a cylindrical bore extending from the left side 12d to the right side 12f of the base 12 may be provided.

A threaded cylindrical bore 16 extends lengthwise from the first end surface 12a to the first cylindrical bore 14. The threaded bore 16 receives a thumb screw (not shown) which tightens down onto the mounting rod 3 to releasably mount the opener 10 on the ring stand support rod.

The cap opener 10 has means on the second end 10b which enables a technician to hold the microcentrifuge tube in one hand, and to open and close the cap of the tube without requiring a second hand. FIGS. 4–22 disclose several embodiments of the single-hand, microcentrifuge tube cap opener of the present invention. FIGS. 4–11 show tube cap openers useful for opening and closing two different standard size tube caps having two different diameters D1,D2. FIGS. 12–20 show tube cap openers useful for opening and closing any size tube cap having a diameter within a range defined by a lower limit D1 and an upper limit D2.

Referring to FIGS. 4–7, the base 12 has a notch 18 formed therein proximate the second end surface 12b. The notch 18 has a horizontal surface 18a extending a distance "Y" generally-parallel to the lengthwise axis of the base. The notch 18 also has a vertical notch surface 18b extending a distance "X" generally-parallel to both end surfaces 12a, 12b.

A first race 20 is formed in the horizontal notch surface 18a. The first race 20 has a width "WR1" slightly larger than the diameter D1 of the first standard size cap. The first race 20 extends lengthwise a distance "Z1" from the second end surface 18b along the entire length of the horizontal notch surface 18a and into the vertical notch surface 18b. The end of the race 20 forms a pocket 22 in the vertical notch surface 18b. The pocket 22 is contiguously formed with the first race 20 and has a length "LP1" which is equal to "Z1" minus "Y" and a width "WP". The length "LP1" of the first pocket 22 is preferably equal to, but may be greater than, the length of the lip of the first cap size. The width "WP" of the first pocket 22 is preferably equal to, but may be larger than, the width of the lip of the first cap size.

A second race 24 is formed in the bottom of the first race 20. The second race 24 has a width "WR2" slightly larger than the diameter of the second standard size cap. The second race 24 extends a distance "Z2" from the second end surface 18b along a lengthwise portion of the first race 20.

The internal end of the second race 24 has a second pocket 26 continuously formed therewith. The second pocket 26 undercuts the bottom surface of the first race 20 and has a length "LP2" which is preferably equal to or greater than the length of the lip of the second cap size.

A cap opener 110 for bubble top snap caps in accordance with the invention is shown in FIGS. 8–11. The cap opener 110 is the same as the cap opener 10 described above except the second race 124 includes a groove 128 extending lengthwise down the center of the second race 124. The groove 128 provides clearance for a cap having an upwardly-extending protrusion 2 or bubble such as seen in FIG. 2.

Figure 12:
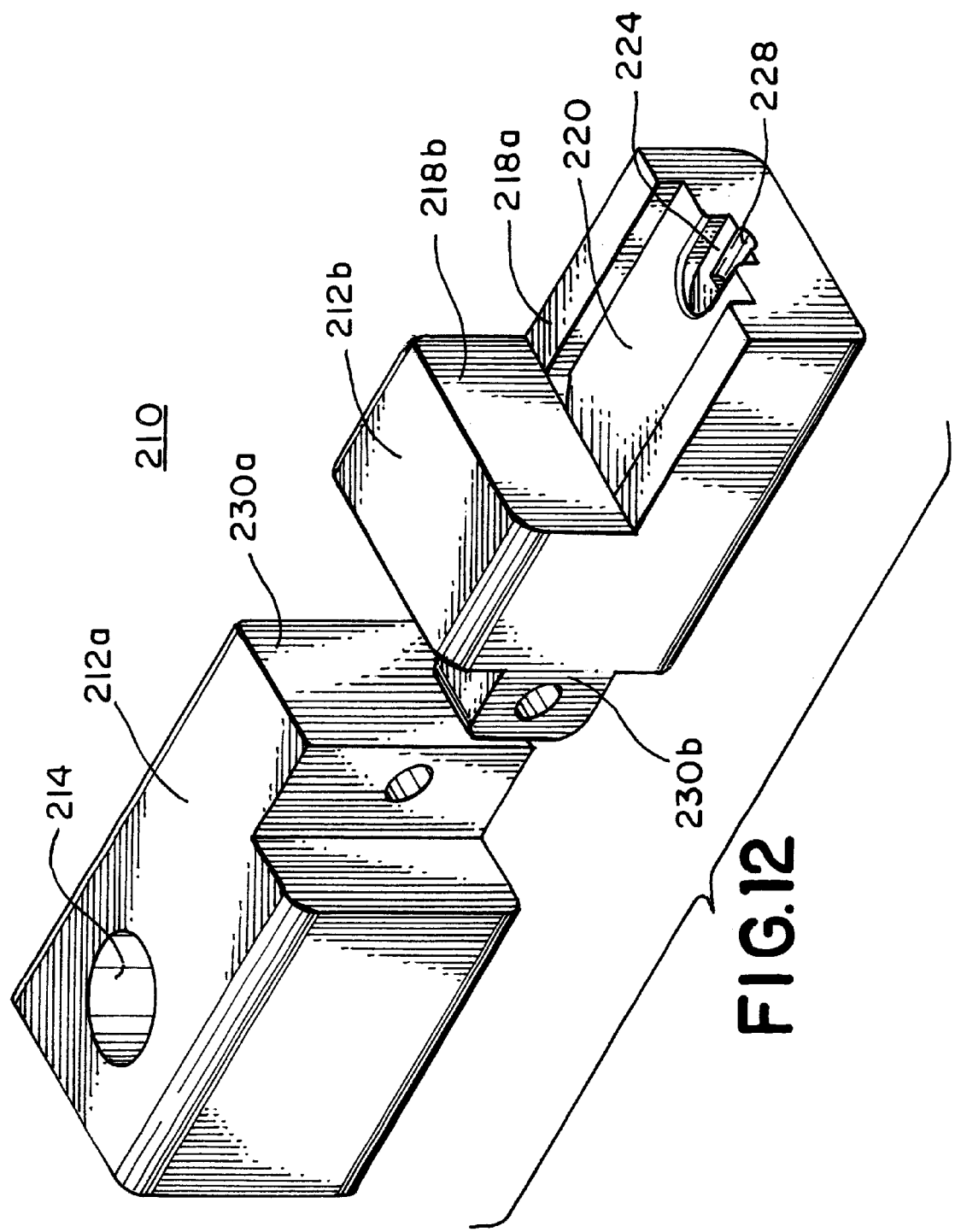
FIG. 12 is a perspective view of a tube cap opener having a split base in accordance with an embodiment of the invention.

A cap opener 210 having a split base 212 in accordance with an embodiment of the invention is shown in FIG. 12. The cap opener 210 is the same as the cap opener described above with reference to FIGS. 8–11 except that the base 212 has a two-part construction. The base halves 212a, 212b are hinged together at a lengthwise intermediate point. The hinge 230 allows the cap opening end of the base to be pivoted upwardly or downwardly relative to the mounting rod 3 of the ring stand for added user comfort.

A cap opener 310 for opening any size cap within a specified size range in accordance with an embodiment of the invention is illustrated in FIGS. 13–16. The construction of the first end of the base 312 used for mounting the opener to a the ring stand is the same as the construction of the first two embodiments 10,110, 210 described above. The elongate base 312 has first 312a and second 312b end surfaces, side surfaces 312c–312f with rounded corners 312g, a first cylindrical bore 314, and a threaded bore 316.

Referring to FIGS. 13–16, the second end of the base 312 has a notch 318 formed therein proximate the second end surface 312b. The notch 318 has a horizontal surface 18a extending a distance "Y" generally-parallel to the lengthwise axis of the base. The notch 318 also has a vertical notch surface 318b extending a distance "X" generally-parallel to both end surfaces 312a, 312b.

Figure 13:
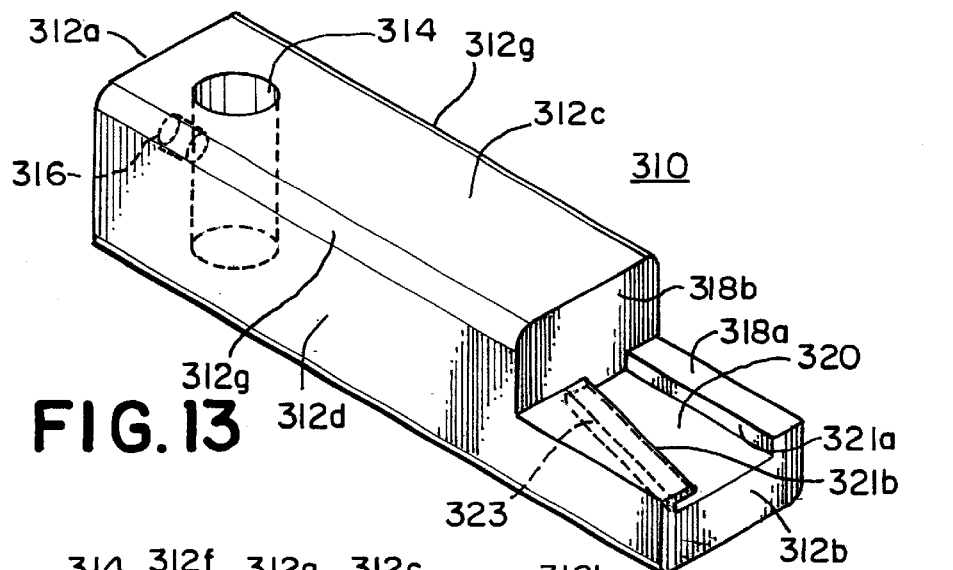
FIG. 13 is a upside-down, perspective view of a single-hand microcentrifuge tube cap opener in accordance with an embodiment of the invention.
Figure 14:
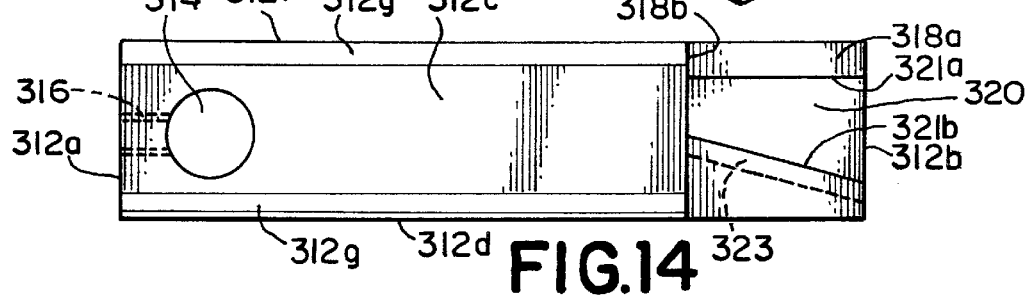
FIG. 14 is a bottom plan view of the tube cap opener shown in FIG. 13.
Figure 15:
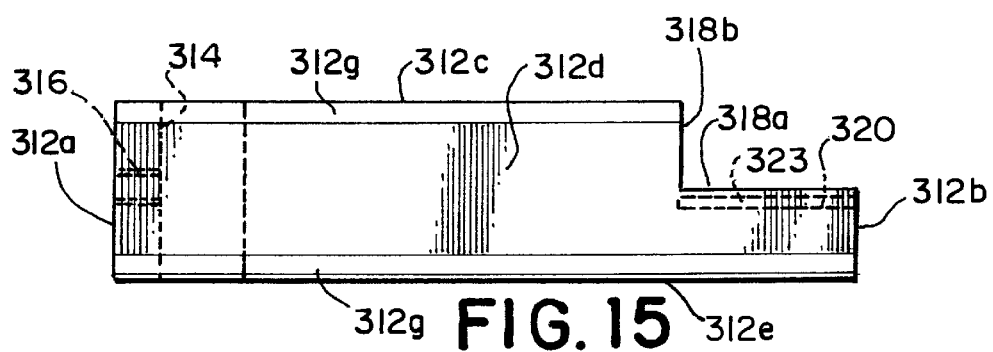
FIG. 15 is an upside-down, side elevational view of the tube cap opener shown in FIG. 13.
Figure 16:
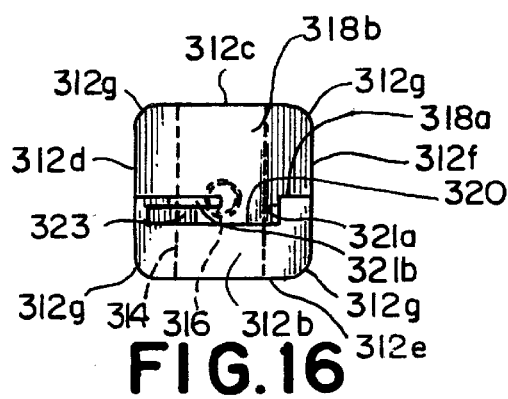
FIG. 16 is an upside-down, front elevational view of the tube cap opener shown in FIG. 13.

A race 320 is formed in the horizontal notch surface 318a. The race 320 extends and converges in width from the second end surface 312b to the vertical notch surface 318b. The race 320 has a planar bottom surface and side walls 321a, 321b generally perpendicular to the bottom surface. One side wall 321a extends parallel to the lengthwise axis of the base 312. The other side wall 321b extends transverse to the lengthwise axis. As best seen in FIG. 13, the width of the race 320 narrows along the length of the base 312 due to the transverse side wall 321b. An undercut groove 323 is formed in the transverse side wall 321b. The undercut groove 323 extends from the second end surface 312b to the vertical notch surface 318b. The undercut groove 323 is coplanar with the bottom surface of the race 320 and extends a depth "DG" into the transverse side wall 321b. Preferably, the depth "DG" of the race is equal to or greater than the length of the lip of the largest cap to be opened.

A cap opener 410 for opening any size cap within a specified range in accordance with another embodiment of the invention is illustrated in FIGS. 17–20. The construction of the mounting end of the base 412 is the same as the construction of the embodiments 10,110,310 described above. The elongate base 412 has first 412a and second 412b end surfaces, side surfaces 412c–412f with rounded corners 412g, a first cylindrical bore 414, and a threaded bore 416. The embodiment illustrated in FIGS. 17–20 has a different means for releasably holding a range of different size caps without holding the tube in which the cap is removably fixed, and allowing the tube to be pivoted about the holding means so that the cap can be pryed from the top of the tube.

Referring to FIGS. 17–20, the second end of the base 412 has a first notch 418 formed therein proximate the second end surface 412b. The first notch 418 has a horizontal surface 418a extending a distance "Y" generally-parallel to the lengthwise axis of the base 412. The first notch 418 also has a vertical notch surface 418b extending a distance "X" generally-parallel to both end surfaces 412a, 412b.

A second notch 430 is formed in the horizontal surface 418a of the first notch 418. The second notch 430 has a horizontal surface extending a distance "Y" from the second end surface 412b to the vertical surface 418b of the first notch 418. The second notch 430 extends widthwise from one side surface 412f to a transverse sidewall 421 intermediate the horizontal surface of the first notch. The second notch 430 extends and converges in width from the second end surface 412b to the vertical surface 418b of the first notch 418. The second notch 430 has a planar bottom surface.

An undercut groove 423 is formed in the transverse side wall 421. The undercut groove 423 extends from the second end surface 412b to the vertical surface 418b of the first notch. The undercut groove 423 is coplanar with the bottom surface of the second notch and extends a depth "DG" into the transverse side wall 421. Preferably, the depth "DG" of the undercut groove is equal to or greater than the length of the lip of the largest ca p to be opened.

Figure 21:
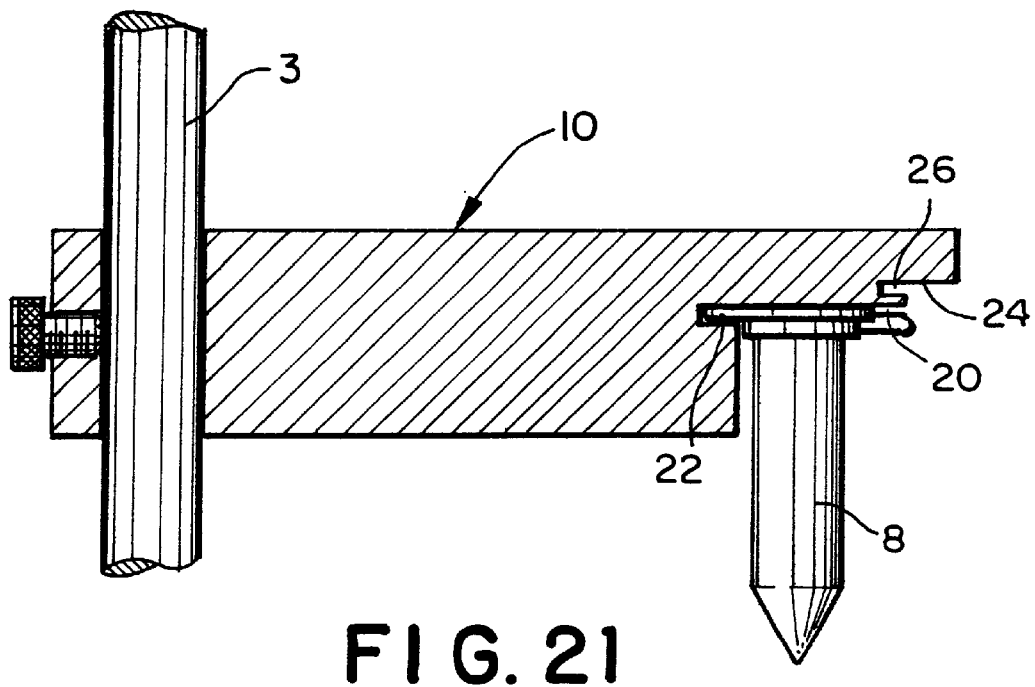
FIG. 21 is a cross-sectional view taken along lines 21—21 of FIG. 3 and a microcentrifuge tube in a closed position; and, FIG. 22 is the tube opener shown in FIG. 22 and a microcentrifuge tube in the open position.
Figure 22:
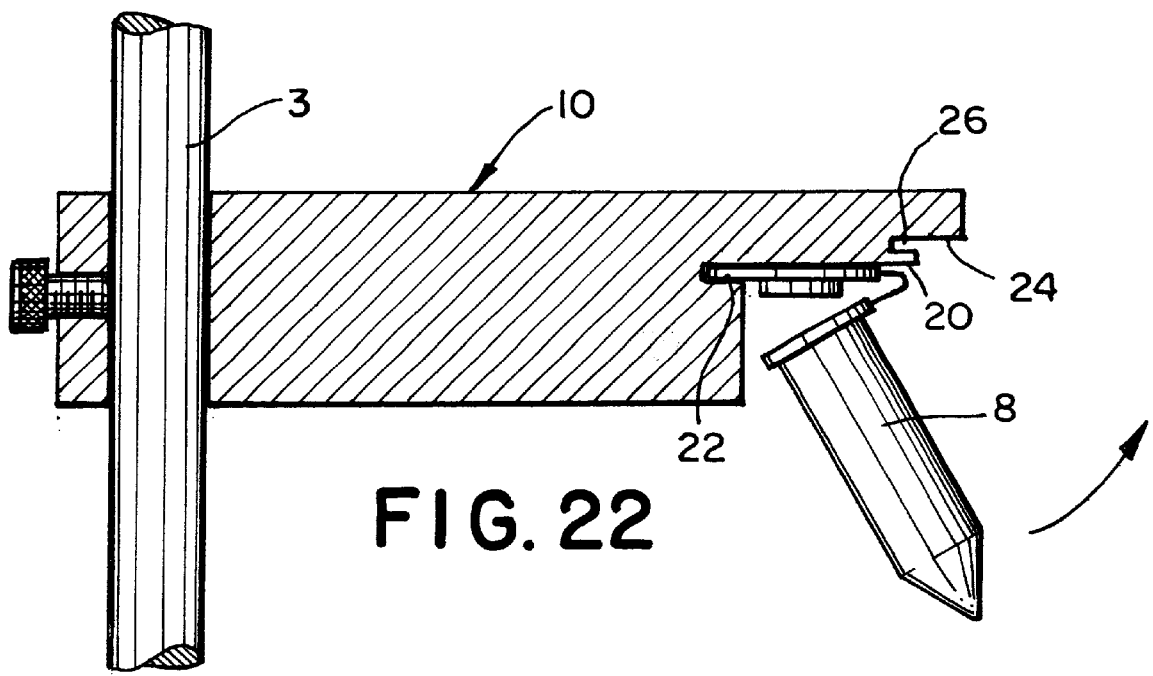

The method of the present invention is described with respect to the apparatus 10 described above and illustrated in FIGS. 3–7. Referring to FIGS. 21 and 21, a microcentrifuge tube is held in one hand by a technician. The cap 6 of the tube 8 is slid into one of the races 20,24 until the lip 9 is inserted into the pocket 22,24 at the end of the race such as shown in FIG. 21. The tube 8 is then rotated upwardly about the cap 6 until the cap 6 is pried open from the tube 8 such as shown in FIG. 22. The cap 6 can be closed by inserting the open cap 6 in a race and pocket and then pushing the tube 8 upwardly until the cap is closed.

What is claimed is:

1. A single-hand apparatus for opening a cap on a microcentrifuge tube, the cap being hinged to the tube and having a radially-protruding lip and a diameter D, comprising:
   a) an elongate base having first and second end surfaces, a plurality of side surfaces extending intermediate said end surfaces, and a lengthwise axis;
   b) a first cylindrical bore proximate said first end surface extending through said base transverse to said lengthwise axis;
   c) a notch in said base proximate said second end surface, said notch having a horizontal surface extending a distance "Y" generally-parallel to said lengthwise axis, and a vertical surface extending a distance "X" generally-parallel to said end surfaces;
   d) a race in said horizontal notch surface extending from said second end surface a distance "Z" which is greater than "Y"; and,
   e) a pocket contiguously formed with the end of said race proximate the intersection of said horizontal and vertical notch surfaces, said pocket having a length "LP1" which is equal to "Z" minus "Y" and a width "WP".

2. The apparatus recited in claim 1, said base comprising an elongate bar having a square cross section.

3. The apparatus recited in claim 1, said first cylindrical bore having a diameter slightly larger than the diameter of the upright support rod of a laboratory ring stand.

4. The apparatus recited in claim 3, including a threaded bore extending from said first end surface to said first cylindrical bore constructed to receive a thumb screw.

5. The apparatus recited in claim 4, including a second cylindrical bore extending through said base transverse to said first bore and said lengthwise axis.

6. The apparatus recited in claim 1, said race having a uniform width "WR1" slightly larger than the diameter D of the cap of the micro-centrifuge tube.

7. The cap opener recited in claim 1, wherein said pocket length "LP1" is approximately equal to or greater than the length of the cap lip.

8. The cap opener recited in claim 1, said base being split into two pivotally-connected halves.

9. A single-hand apparatus which allows a technician to hold different size microcentrifuge tube caps, each cap having a diameter D and a radially-protruding lip, comprising;
   a) an elongate base having first and second end surfaces, a plurality of side surfaces extending intermediate said end surfaces, and a lengthwise axis;
   b) means on the first end for mounting said base at any location along the length of the support rod of a laboratory ring stand; and,
   c) means on said base for allowing a technician to hold the microcentrifuge tube in one hand, and to open and close the cap without requiring a second hand.

10. The apparatus recited in claim 9, said means for allowing including:
    d) first means on the second end for releasably holding a first size cap without holding the tube; and,
    e) second means on the second end for releasably holding a second size cap without holding the tube.

11. The apparatus recited in claim 10, said first holding means comprising a notch in said base proximate said second end surface, said notch having a horizontal surface extending a distance "Y" generally-parallel to said lengthwise axis, and a vertical surface extending a distance "X" generally-parallel to said end surfaces.

12. The apparatus recited in claim 11, including:
    a) a first race in said horizontal notch surface extending from said second end surface a distance "Z1" which is greater than "Y"; and,
    b) a first pocket contiguously formed with said race proximate the intersection of said horizontal and vertical notch surfaces, said pocket having a length "LP1" which is equal to "Z" minus "Y" and a width "WP".

13. The apparatus recited in claim 12, said first race having a width "WR1" slightly larger than the diameter D1 of the first size cap.

14. The apparatus recited in claim 13, wherein said first pocket length "LP1" is approximately equal to or greater than the length of the lip of the first size cap.

15. The apparatus recited in claim 14, said second holding means comprising:
    a) a second race formed in said first race, said second race extending from said second end surface a distance "Z2" which is less than "Y"; and,
    b) a second pocket contiguously formed with the end of said first race intermediate the said horizontal notch surface, said pocket having a length "LP2".

16. The apparatus recited in claim 15, said second race having a width "WR1" slightly larger than the diameter D2 of the second size cap.

17. The apparatus recited in claim 16, wherein said second pocket length "LP2" is approximately equal to or greater than the length of the lip of the second size cap.

18. The apparatus recited in claim 17, including a groove extending lengthwise down the center of said second race.

19. The apparatus recited in claim 9, said mounting means comprising a cylindrical bore proximate said first end surface extending through said base transverse to said lengthwise axis.

20. The apparatus recited in claim 19, including a second cylindrical bore extending through said base transverse to said first bore and said lengthwise axis.

21. A single-hand apparatus for opening and closing any size mricocentifuge cap within a specified size range, each cap having a diameter D and a radially-protruding lip, comprising:

a) an elongate base having first and second end surfaces, a plurality of side surfaces extending intermediate said end surfaces, and a lengthwise axis;

b) a cylindrical bore proximate said first end surface extending through said base transverse to said lengthwise axis;

c) means on the second end for releasably holding a range of different size caps without holding the tube in which the cap is removably fixed; and, d) means for allowing the tube to be pivoted about the holding means so that the cap is pried open from the top of the tube.

22. The apparatus recited in claim 21, said mounting means comprising a cylindrical bore proximate said first end surface extending through said base transverse to said lengthwise axis.

23. The apparatus recited in claim 22, including a second threaded bore extending from said first end surface to said cylindrical bore.

24. The apparatus recited in claim 21, said holding means comprising:

a) a notch in said base proximate said second end surface, said notch having a horizontal surface extending a distance "Y" generally-parallel to said lengthwise axis, and a vertical surface extending a distance "X" generally-parallel to said end surfaces;

b) a race in said horizontal notch surface extending and converging in width from said second end surface to said vertical notch surface, said race having a planar bottom surface and side walls generally perpendicular to said bottom surface; and, c) an undercut grove in one of the side walls of said race.

25. The apparatus recited in claim 24, said undercut groove extending from said second end surface to said vertical notch surface.

26. The apparatus recited in claim 25, one of said race side walls extending parallel to said lengthwise axis, the other race sidewall extending transverse to said lengthwise axis.

27. The apparatus recited in claim 26, said undercut groove being formed in the transverse extending race sidewall.

28. The apparatus recited in claim 27, said undercut groove being coplanar with said race bottom surface.

29. The apparatus recited in claim 28, said undercut groove extending a depth D into said sidewall, said depth D being greater than or equal to the length of the lip of the cap.

30. The apparatus recited in claim 21, said holding means comprising:

a) a first notch in said base proximate said second end surface, said first notch having a horizontal surface extending a distance "Y" generally-parallel to said lengthwise axis, and a vertical surface extending a distance "X" generally-parallel to said end surfaces;

b) a second notch in said horizontal notch surface, said second notch having a horizontal surface extending lengthwise a distance "Y" from said second end surface to the vertical surface of said first notch, and extending widthwise a from one of said base side surfaces to a side wall intermediate the horizontal surface of said first notch; and, c) a n undercut grove in the side wall of said second notch.

31. The apparatus recited in claim 30, said second notch converging in width from said second end surface to the vertical surface of said first notch.

32. The apparatus recited in claim 31, said second notch having a planar bottom surface.

33. The apparatus recited in claim 32, said undercut groove being coplanar with said second notch bottom surface.

34. The apparatus recited in claim 33, said undercut groove extending a depth D into said sidewall, said depth D being greater than or equal to the length of the lip of the cap.

35. A method of opening and closing a cap on a microcentrifuge tube using only one hand, comprising the steps of:

a) providing a single-hand tube cap opener, comprising:
  i) an elongate base having first and second end surfaces, a plurality of side surfaces extending intermediate said end surfaces, and a lengthwise axis;
  ii) a cylindrical bore proximate said first end surface extending through said base transverse to said lengthwise axis; and,
  iii) means for allowing a technician to hold the microcentrifuge tube in one hand, and to open and close the cap without requiring a second hand;

b) grasping the microcentrifuge tube with a first hand;

c) engaging the cap of the tube with said single-hand tube cap opener by using only the first hand; and, d) pivoting the tube with the first hand about the cap until the cap is pried open from the tube.

* * * * *